United States Patent [19]

Liversidge et al.

[11] Patent Number: 5,552,160

[45] Date of Patent: *Sep. 3, 1996

[54] SURFACE MODIFIED NSAID NANOPARTICLES

[75] Inventors: Gary G. Liversidge; Philip Conzentino, Jr., both of West Chester; Kenneth C. Cundy, Pottstown; Pramod P. Sarpotdar, Malvern, all of Pa.

[73] Assignee: NanoSystems L.L.C., Collegeville, Pa.

[ * ] Notice: The term of this patent shall not extend beyond the expiration date of Pat. No. 5,145,684.

[21] Appl. No.: 402,662

[22] Filed: Mar. 13, 1995

Related U.S. Application Data

[63] Continuation of Ser. No. 897,193, Jun. 10, 1992, abandoned, which is a continuation-in-part of Ser. No. 647,105, Jan. 25, 1991, Pat. No. 5,145,684.

[51] Int. Cl.$^6$ .................................................. A61K 9/14
[52] U.S. Cl. .......................... 424/489; 424/450; 424/495; 424/499
[58] Field of Search ..................................... 424/489, 450, 424/499, 495

[56] References Cited

U.S. PATENT DOCUMENTS

| | | | |
|---|---|---|---|
| 2,996,433 | 8/1961 | Hoppe et al. | 424/9.411 |
| 3,192,118 | 6/1965 | Battista et al. | 424/9.411 |
| 4,255,581 | 9/1980 | Kreuter et al. | 424/280.1 |
| 4,269,821 | 5/1981 | Kreuter et al. | 424/489 |
| 4,826,689 | 5/1989 | Violante et al. | 424/489 |
| 4,918,103 | 4/1990 | Park et al. | 514/520 |
| 4,944,949 | 7/1990 | Story et al. | 424/455 |
| 5,018,370 | 5/1991 | Jay et al. | 66/55 |
| 5,091,188 | 2/1992 | Haynes | 424/450 |
| 5,110,493 | 5/1992 | Chern-Chyi et al. | 514/413 |
| 5,112,868 | 5/1992 | Cetenko et al. | 514/398 |
| 5,145,684 | 9/1992 | Liversidge et al. | 424/489 |

FOREIGN PATENT DOCUMENTS

| | | |
|---|---|---|
| 0371431 | 6/1990 | European Pat. Off. . |
| 0424028 | 11/1990 | European Pat. Off. . |
| 0437083 | 12/1990 | European Pat. Off. . |
| 0499299A2 | 8/1992 | European Pat. Off. . |
| 91/06292 | 5/1991 | WIPO . |
| 92/00725 | 1/1992 | WIPO . |

OTHER PUBLICATIONS

Cioli et al, Tox. and Appl. Pharm., 50, 283–289 (1979) The Role of Direct Tissue Contact in the Production of Gastrointestinal Ulcers by Anti–Inflammatory Drugs in Rats.

Price et al, Drugs, 40, (Suppl. 5):1–11 (1990) Mechanisms of NSAID-Induced Gastroenteropathy.

Aabakken et al, 65–73, Comparison of the Gastrointestinal Side Effects of Naproxen Formulated as Plain Tablets, Enteric–Coated Tablets, or Enteric–Coated Granules in Capsules.

Gursoy et al "Evaluation of Indomethacin Nanocapsules for their Physical Stability and Inhibitory Activaty on Inflammation and Platelet Aggregation" Chemical Abstracts, vol. 111, No. 8, 1989 pp. 101–108.

Primary Examiner—Thurman K. Page
Assistant Examiner—William E. Benston, Jr.
Attorney, Agent, or Firm—Rudman & Balogh

[57] ABSTRACT

Dispersible particles consisting essentially of a crystalline NSAID having a surface modifier adsorbed on the surface thereof in an amount sufficient to maintain an effective average particle size of less than about 400 nm. Pharmaceutical compositions containing the particles exhibit reduced gastric irritation following oral administration and/or hastened onset of action.

13 Claims, No Drawings

SURFACE MODIFIED NSAID NANOPARTICLES

This application is a continuation of U.S. patent application Ser. No. 07/897,193, filed Jun. 10, 1992, now abandoned, which was a continuation-in-part of U.S. patent application Ser. No. 647,105, filed Jan. 25, 1991, now U.S. Pat. No. 5,145,684, issued Sep. 8, 1992.

BACKGROUND OF INVENTION

Nonsteroidal anti-inflammatory drugs (NSAIDs) are one of the most commonly used and therapeutically effective groups of drugs. However, gastric irritation problems constitute the most frequently recognized adverse side effect following oral administration of NSAIDs. Such side effects are well recognized and must be weighed against the clinical efficacy of the drugs.

A great amount of research has been undertaken in an attempt to understand the underlying mechanism responsible for these effects. For example, Cioli et al, *Tox. and Appl. Pharm.*, 50, 283–289 (1979) suggest that gastrointestinal lesions in laboratory animals resulting from the oral administration of acidic NSAIDs may depend on two different mechanisms: a local action exerted by contact with the gastric mucosa and a generalized/centrally mediated (systemic) action, taking place following oral administration.

More recently, Price et al, *Drugs* 40 (Suppl. 5):1–11, 1990, suggest that NSAID-induced gastric damage occurs as a result of NSAID-mediated direct and indirect acidic damage followed almost simultaneously by the deleterious systemic effect of prostaglandin inhibition.

A variety of strategies have been used in the management of NSAID-induced gastric damage. These include: 1) the development and use of NSAIDs with less toxic potential; 2) the reduction or elimination of the agent that actually causes the injury; and 3) the enhancement of the mucosal defense. However, these approaches have not proven entirely successful.

For example, the most effective means of preventing gastric damage, i.e., by eliminating the primary aetiological agent is rarely feasible with NSAIDs inasmuch as patients with severe inflammatory disease are rarely able to cease using these drugs. Although selection of less toxic NSAIDs should prove useful, the only practical solution, at present, is to treat the NSAID induced gastric damage. Misoprostol (a methylated prostaglandin $E_1$) has been approved by the FDA for use in preventing NSAID gastropathy. However, Misoprostol is expensive, must be administered multiple times daily and can cause unacceptable side effects.

Thus it would be highly desirable to provide NSAID formulations that can exhibit a reduction in gastric irritation. Moreover, it would be desirable to provide NSAID formulations exhibiting hastened onset of action.

SUMMARY OF THE INVENTION

We have discovered that pharmaceutical compositions containing surface modified NSAID nanoparticles exhibit reduced gastric irritation following oral administration and/or more rapid onset of action.

More particularly, in accordance with this invention, there are provided particles consisting essentially of an NSAID having a surface modifier adsorbed on the surface thereof in an amount sufficient to maintain an average particle size of less than about 400 nm.

This invention further provides a pharmaceutical composition comprising the above-described particles and a pharmaceutically acceptable carrier.

In another embodiment of the invention, there is provided a method of treating a mammal comprising administering to the mammal the above-described pharmaceutical composition.

In yet another embodiment of the invention, there is provided a method of preparing the above-described particles comprising the steps of dispersing an NSAID in a liquid dispersion medium and wet grinding the NSAID in the presence of rigid grinding media, wherein the pH of said medium is maintained within the range of from 2 to 6.

In further embodiments of the invention, there are provided methods of reducing gastric irritation and/or hastening the onset of action which include administering the above-described pharmaceutical composition to a mammal.

It is an advantageous feature of this invention that pharmaceutical compositions containing NSAIDs are provided which exhibit reduced gastric irritation following oral administration.

It is another advantageous feature of this invention that pharmaceutical compositions are provided exhibiting hastened onset of action.

Other advantageous features will become readily apparent upon reference to the following description of preferred embodiments.

DESCRIPTION OF THE PREFERRED EMBODIMENTS

This invention is based partly on the discovery that surface modified nanoparticles comprising an NSAID, e.g., naproxen, demonstrate reduced gastric irritation and/or a more rapid onset of action following oral administration. While the invention is described herein primarily in connection with its preferred class of drugs, i.e., NSAIDs, it is also useful in conjunction with other classes of drug substances, e.g., antibiotics, quinolones, antilipemics and roentgenographics.

The particles of this invention comprise an NSAID. The NSAID exists as a discrete, crystalline phase. The crystalline phase differs from an amorphous or non-crystalline phase which results from conventional solvent precipitation techniques, such as described in U.S. Pat. No. 4,826,689. The NSAID can be present in one or more suitable crystalline phases.

The invention can be practiced with a wide variety of NSAIDs. However, the NSAID must be poorly soluble and dispersible in at least one liquid medium. By "poorly soluble" it is meant that the NSAID has a solubility in the liquid dispersion medium, e.g., water, of less than about 10 mg/ml, and preferably of less than about 1 mg/ml at processing temperature, e.g., room temperature. The preferred liquid dispersion medium is water. However, the invention can be practiced with other liquid media in which the NSAID is poorly soluble and dispersible including, for example, aqueous salt solutions, safflower oil and solvents such as ethanol, t-butanol, hexane and glycol. The pH of the aqueous dispersion media can be adjusted by techniques known in the art.

The NSAIDs useful in the practice of this invention can be selected from suitable acidic and nonacidic compounds.

Suitable acidic compounds include carboxylic acids and enolic acids. Suitable nonacidic compounds include, for example, nabumetone, tiaramide, proquazone, bufexamac, flumizole, epirazole, tinoridine, timegadine and dapsone.

Suitable carboxylic acid NSAIDs include, for example, salicylic acids and esters thereof, such as aspirin, phenylacetic acids such as diclofenac, alclofenac and fenclofenac, and carbo- and heterocyclic acetic acids such as etodolac, indomethacin, sulindac, tolmetin, fentiazac and tilomisole; propionic acids, such as carprofen, fenbufen, flurbiprofen, ketoprofen, oxaprozin, suprofen, tiaprofenic acid, ibuprofen, naproxen, fenoprofen, indoprofen, pirprofen; and fenamic acids, such as flufenamic, mefenamic, meclofenamic and niflumic.

Suitable enolic acid NSAIDs include, for example, pyrazolones such as oxyphenbutazone, phenylbutazone, apazone and feprazone, and oxicams such as piroxicam, sudoxicam, isoxicam and tenoxicam.

The above-described NSAIDs are known compounds and can be prepared by techniques known in the art.

In particularly preferred embodiments of the invention, the NSAID is naproxen, indomethacin or ibuprofen.

The particles of this invention contain an NSAID as described above having a surface modifier adsorbed on the surface thereof. Useful surface modifiers are believed to include those which physically adhere to the surface of the NSAID but do not chemically bond to the NSAID.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), and polyvinylpyrrolidone (PVP). Most of these excipients are described in detail in the *Handbook of Pharmaceutical Excipients*, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone, tyloxapol, polaxomers, such as Pluronic™ F68 and F108, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylenediamine available from BASF, dextran, lecithin, Aerosol OT™, which is a dioctyl ester of sodium sulfosuccinic acid, available from American Cyanamid, Duponol™ P, which is a sodium lauryl sulfate, available from DuPont, Triton™ X200, which is an alkyl aryl polyether sulfonate, available from Rohm and Haas, Tween 20 and Tween 80, which are polyoxyethylene sorbitan fatty acid esters, available from ICI Speciality Chemicals, Carbowax™ 3550 and 934, which are polyethylene glycols available from Union Carbide, Crodesta™ F-110, which is a mixture of sucrose stearate and sucrose distearate, available from Croda Inc., Crodesta SL-40, which is available from Croda, Inc., and SA90HCO, which is $C_{18}H_{37}$-$CH_2$(CON $(CH_3)CH_2(CHOH)_4CH_2OH)_2$. Surface modifiers which have been found to be particularly useful include polyvinylpyrrolidone, Pluronic F-68, and lecithin.

The surface modifier is adsorbed on the surface of the NSAID in an amount sufficient to maintain an effective average particle size of less than about 400 nm. The surface modifier does not chemically react with the NSAID or itself. Furthermore, the individually adsorbed molecules of the surface modifier are essentially free of intermolecular crosslinkages.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a number average particle size of less than about 400 nm when measured by the above-noted techniques. In preferred embodiments of the invention, the effective average particle size is less than about 300 nm. With reference to the effective average particle size, it is preferred that at least 95% and, more preferably, at least 99% of the particles have a particle size of less than the effective average, e.g., 400 nm. In particularly preferred embodiments, essentially all of the particles have a size less than 400 nm.

The particles of this invention can be prepared in a method comprising the steps of dispersing an NSAID in a liquid dispersion medium and applying mechanical means in the presence of grinding media to reduce the particle size of the NSAID to an effective average particle size of less than about 400 nm. The particles can be reduced in size in the presence of a surface modifier. Alternatively, the particles can be contacted with a surface modifier after attrition.

A general procedure for preparing the particles of this invention is set forth below. The NSAID selected is obtained commercially and/or prepared by techniques known in the art in a conventional coarse form. It is preferred, but not essential, that the particle size of the coarse NSAID selected be less than about 100 μm as determined by sieve analysis. If the coarse particle size of the NSAID is greater than about 100 μm, then it is preferred that the particles of the NSAID be reduced in size to less than 100 μm using a conventional milling method such as airjet or fragmentation milling.

The coarse NSAID selected can then be added to a liquid medium in which it is essentially insoluble to form a premix. The concentration of the NSAID in the liquid medium can vary from about 0.1–60%, and preferably is from 5–30% (w/w). It is preferred, but not essential, that the surface modifier be-present in the premix. The concentration of the surface modifier can vary from about 0.1 to about 90%, and preferably is 1–75%, more preferably 20–60%, by weight based on the total combined weight of the drug substance and surface modifier. The apparent viscosity of the premix suspension is preferably less than about 1000 centipoise.

The premix can be used directly by subjecting it to mechanical means to reduce the average particle size in the dispersion to less than 400 nm. It is preferred that the premix be used directly when a ball mill is used for attrition. Alternatively, the NSAID and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the NSAID conveniently can take the form of a dispersion mill. Suitable dispersion mills include a ball mill, an attritor mill, a vibratory mill, a planetary mill, media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, zirconium oxide, such as 95% ZrO stabilized with magnesia, zirconium silicate, and glass grinding media provide particles having levels of contamination which are believed to be acceptable for the preparation of pharmaceutical compositions. Further, other media, such as stainless steel, titania, alumina, and 95% ZrO stabilized with yttrium, are expected to be useful. Preferred media have a density greater than about 2.5 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the NSAID. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

Milling must be carried out under acidic conditions, at a pH of from 2–6, preferably 3–5. The preferred pH depends, e.g., on the acidity and solubility of the particular NSAID selected. Acid resistant milling equipment is highly preferred, e.g., equipment fabricated of high grade stainless steel, e.g., grade 316 SS, or equipment coated with an acid resistant coating.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of the NSAID and surface modifier can vary widely and the optimal amount of the surface modifier can depend, for example, upon the particular NSAID and surface modifier selected, the critical micelle concentration of the surface modifier if it forms micelles, the surface area of the NSAID, etc. The surface modifier preferably is present in an amount of about 0.1–10 mg per square meter surface area of the NSAID. The surface modifier can be present in an amount of 0.1–90%, preferably 0.5–80%, and more preferably 1–60% by weight based on the total weight of the dry particle.

A simple screening process has been developed whereby compatible surface modifiers and NSAIDs can be selected which provide stable dispersions of the desired particles. First, coarse particles of an NSAID are dispersed in a liquid in which the NSAID is essentially insoluble, e.g., water at 5% (w/v) and milled for 120 hours in a roller mill under the following milling conditions:

Grinding vessel: 8 oz. (250 ml) glass jar

Available volume of grinding vessel: 250 ml

Media volume: 120 ml

Media type: 1.0 mm pre-cleaned zirconium oxide beads (distributed by Zircoa, Inc.)

Milling time: 120 hours

Slurry volume: 60 ml

RPM: 92

Room Temperature pH: 4.0 (adjusted with HCl or NaOH, if necessary)

The slurry is separated from the milling media by conventional means, e.g., by pouring the slurry out of the vessel, or by using a pipette. The separated slurry is then divided into aliquots and surface modifiers are added at a concentration of between 2 and 50% by weight based on the total combined weight of the NSAID and surface modifier. The dispersions are then sonicated (1 minute, 20 kHz) or vortexed using a multitubed vortexer for one minute, to disperse agglomerates and subjected to particle size analysis, e.g., by photon correlation spectroscopy and/or by examination under an optical microscope (1000× magnification). If a stable dispersion is observed, then the process for preparing the particular NSAID surface modifier combination can be optimized in accordance with the teachings above. By stable it is meant that the dispersion exhibits no flocculation or particle agglomeration visible to the naked eye and, preferably, when viewed under the optical microscope at 1000×, at least 15 minutes, and preferably, at least two days or longer after preparation. In addition, preferred particles exhibit no flocculation or agglomeration when dispersed in 0.1N HCl or simulated GI fluid (USP).

The resulting dispersion is stable and consists of the liquid dispersion medium and the above-described particles. The dispersion of surface modified NSAID nanoparticles can be spray coated onto sugar spheres or onto a pharmaceutical excipient in a fluid-bed spray coater by techniques well known in the art.

Pharmaceutical compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the NSAID for treatment is effective to obtain a desired therapeutic response for a particular composition and method of administration. The selected dosage level therefore, depends upon the particular NSAID, the desired therapeutic effect, on the route of administration, on the desired duration of treatment and other factors.

It is a particularly advantageous feature that the pharmaceutical compositions of this invention exhibit reduced gastric irritation and/or more rapid onset of action as illustrated in the examples that follow.

The following examples further illustrate the invention.

Example 1

A nanoparticulate naproxen dispersion (Formula 1) was prepared in a roller mill as follows. A 250 ml glass jar was charged with 120 ml of 1.0 mm pre-cleaned Zirconium oxide beads (Zirbeads XR, available from Zircoa Inc., having a nominal diameter of 1.0 mm), 60 g of an aqueous slurry containing 3 g naproxen (5% by weight), purchased from Sigma, St. Louis, Mo., particle size 20–30 μm, and 1.8 g (3% by weight) Pluronic F-68, purchased from BASF Fine Chemicals, Inc., as the surface modifier. The beads were pre-cleaned by rinsing in 1N $H_2SO_4$ overnight followed by several rinses with deionized water. The batch was rolled at 92 RPM for a total of 120 hours. The dispersion was stable when a portion was added to 0.1N HCl. The average particle size measured by photon correlation spectroscopy was 240–300 nm.

A control formulation of naproxen was prepared by adding 5% (w/v) unmilled naproxen to 3% Pluronic F-68. The suspension was vortexed and sized. The particle size range was 20–30 μm.

The concentration of naproxen in both formulations was 50 mg/mL (w/v). Both formulations were diluted with 3% Pluronic F-68 to a dosing concentration of 10 mg/mL for oral administration.

Male Sprague-Dawley rats were maintained in accordance with the conditions set forth in "Guide for the Care and Use of Laboratory Animals", NIH Publication 86-23 The temperature was maintained at 22±1° C. and the relative humidity was 50±10%, with a 12 hour light/dark cycle. Rats were provided laboratory chow and water. The rats (250–350 g) were anesthetized with a 55 mg/kg intraperitonal injection of Nembutal (sodium pentobarbital). The external Jugular veins were chronically cannulated to facilitate removal of blood samples. Prior to administration of naproxen, the rats were allowed to recover for 24 hours with water ad libitum.

The rats were anesthetized, with Metofane, orally gavaged with the above-described formulations and placed in a restraint device. Blood samples (100 μl) were obtained via the jugular vein at 0 (pre-administration), 5, 10, 15, 30, 45, 60, 75, 90, 120, 180 and 240 minutes following administration of naproxen and collected in heparinized tubes. Plasma (50 μl) was obtained immediately and placed on ice. Plasma samples (50 μl) were mixed with 130 μl of acetonitrile and 20 μl of a standard solution (20 μg/ml indomethacin) and vortexed to precipitate protein. Samples were centrifuged and the supernatants removed, placed in vials, and analyzed by HPLC. The Separation of naproxen was carried out on an analytical column (Waters Novapak C18; 15 cm×4 mm, 5μ).

At the end of the experiment (240 min.) the rats were euthanized by an I.V. bolus injection of Nembutal via the jugular vein. The stomachs were removed and cut along the line of greater curvature from the duodenum to the pyloric sphincter. The stomachs were then spread flat and pinned out on dissecting dishes, and washed with 0.9% NaCl.

The evaluation and counting of stomach irritations (erosion/lesion/ulcer) were conducted by a modification of arbitrary scoring systems (Cioli et al, *Tox. and Appl. Pharm.*, 1979, 50:283–289 and Beck et al, *Arch. Toxicol.*, 1990; 64:210–217) correcting for various degrees of severity as noted below. Differences in severity index have been associated with the gastropathology present on the stomach following oral administration of NSAIDs (Balaa, *Am. Journ. Med. Sci.*, 1991, 301:272–276 and Lanza et al; *Dig. Dis. and Sci.*, 1990; 35:12).

Each stomach irritation was measured in length (or diameter) using a 10 mm surgical ruler. The length of the irritations ranged from 0.25 mm to 10.0 mm. Irritations less than 0.25 mm were classified as pinpoint. The irritations were categorized by color as an evaluation of severity. Irritations red in appearance were rated as mild and assigned a severity value of 1. Brown irritations were rated as moderately severe and assigned a value of 2. Irritations which appeared black were rated as the most severe and given a severity value of 3. A score for each irritation was determined by multiplying the length value and the point severity level. The sum total for all irritations on a given stomach was identified as the total irritation score.

Table 1 shows the mean values for the stomach irritations induced by naproxen in the Control formulation and Formulation 1 of this invention. As indicated by the data, the formulation of this invention exhibited a reduction in stomach irritation scores compared to the control (p=0.099). It was concluded that the formulation of this invention exhibits reduced gastric irritation following oral administration as compared to the control.

TABLE 1

| Rat No. | Control (n = 6) | Formulation 1 (n = 8) |
|---------|-----------------|------------------------|
| 1       | 293             | 43                     |
| 2       | 200             | 139                    |
| 3       | 133             | 149                    |
| 4       | 140             | 80                     |
| 5       | 110             | 129                    |
| 6       | 101             | 163                    |
| 7       |                 | 54                     |
| 8       |                 | 98                     |
| Mean    | 163             | 107                    |
| SEM     | 30              | 16                     |

Surprisingly, the formulation of this invention when administered orally induced a similar level of gastric irritation compared to the same formulation administered parenterally, i.e., I.V. Thus, the formulation of this invention appears virtually devoid of a direct irritant effect on the stomach of a rat.

A statistical comparison of the pharmacokinetic plasma parameters Cmax (peak plasma concentration), Tmax (time to peak plasma concentration) and relative bioavailability ($AUC_{(0-240\ min)}$—from Area Under the Curve values from 0–240 minutes) for Formulation 1 of this invention and the control calculated by the trapezoidal method is set forth below.

|  | Mean ± SEM | |
| --- | --- | --- |
|  | Control | Formulation 1 |
| Cmax (µg/ml) | 126 ± 4 (n = 5) | 187 ± 19 (n = 6) |
| Tmax (min) | 34 ± 3 (n = 5) | 24 ± 5 (n = 6) |
| AUC$_{(0-240\ min)}$ (µg × min/ml) | 15,228 ± 994 (n = 5) | 19,062 ± 573 (n = 3) |

The data indicate that the time to peak plasma concentration were lower for the formulation of this invention compared to the control (p=0.15) and both the relative bioavailability and peak plasma concentrations were significantly higher for the formulation of this invention compared to the control (p=0.03) and (p=0.02), respectively. The increase in apparent rate of absorption clearly suggests enhanced onset of action.

Example 2

The preparation of Example 1 was repeated except that 5% by weight polyvinylpyrrolidone was used in place of the Pluronic F-68. The average particle size was 250 mm.

Examples 3–8 illustrate the preparation of nanoparticulate ibuprofen.

Example 3

Nanoparticulate ibuprofen was prepared in a planetary mill (Pulverisette-7, manufactured by Fritsch, Gmbh) containing two 25 ml bowls. The initial charge (per bowl) included 12.5 ml of 1 mm pre-cleaned zirconium oxide beads and 6.25 ml of an aqueous slurry containing 100 mM HCl, 3% (w/v) ibuprofen, and 2% (w/v) Pluronic F-68 as the surface modifier. The ibuprofen formulation was milled for 24 hours at 325 RPM. The resulting dispersion was stable when a portion was added to simulated gastric fluid, i.e., 2 g NaCl, 3.2 g pepsin, 7 ml HCl, and $H_2O$ to 1 liter, pH=1.2. The average particle size measured by photon correlation spectroscopy was 253 nm.

Example 4

Example 3 was repeated except that the initial charge included 1% Tween 20 and the milling time was 17 hours. The average particle size was 263 nm.

Example 5

Example 3 was repeated except that the milling time was 4 hours. The average particle size was 314 nm.

Example 6

Example 3 was repeated except that the surface modifier in the initial charge was 1% (w/v) of a 1:2 by weight mixture of Tween 20 and Span 20, and the milling time was 20 hours at 175 RPM. The average particle size was 294 nm.

Example 7

Example 3 was repeated except that the initial charge included 0.25% (w/v) tyloxapol as the surface modifier and 10 mM HCl. The charge was milled for 20 hours at 175 RPM in a refrigerated (5° C.) area. The average particle size was 344 nm.

Example 8

Example 7 was repeated except that Tween 20 was used in place of the tyloxapol. The average particle size was 351 nm.

Examples 9–12 illustrate the preparation of nanoparticulate indomethacin.

Example 9

Nanoparticulate indomethacin was prepared in a roller mill as follows. A 250 ml bottle was charged with 125 ml of 1.0 mm pre-cleaned $ZrO_2$ beads, 200 gm of an aqueous slurry containing 10 gms indomethacin (5% by weight) and 2 gms Vinol 205, a polyvinylalcohol (1% by weight). A batch size of 200 gms was used to reduce air space in the bottle to minimize the formation of foam. The batch was rolled at 88.5 RPM for a total of 240 hours. The dispersion was stable in 0.1N HCl and simulated gastric fluid as described in Example 3 above. The average particle size measured by photon correlation spectroscopy was 331 nm.

Example 10

Example 9 was repeated except that polyvinylpyrrolidone was used in place of the polyvinylalcohol. The average particle size was 216 nm.

Example 11

Example 9 was repeated except that Pluronic F-68 was used in place of the polyvinylalcohol. The average particle size was 228 nm.

Example 12

Example 9 was repeated except that Pluronic F-108 was used in place of the polyvinylalcohol. The average particle size was 235 nm.

The invention has been described in detail with particular reference to certain preferred embodiments thereof, but it will be understood that variations and modifications can be effected within the spirit and scope of the invention.

What is claimed is:

1. Particles consisting essentially of 99.9–10% by weight of crystalline NSAID having a solubility in water of less than 10 mg/ml, said NSAID having a non-crosslinked surface modifier adsorbed on the surface thereof in an amount of 0.1–90% by weight and sufficient to maintain an average particle size of less than about 400 nm.

2. The particles of claim 1 having an effective average particle size of less than 300 nm.

3. The particles of claim 1 wherein said surface modifier is present in an amount of 0.5 to 80% by weight based on the total weight of the dry particle.

4. The particles of claim 1 wherein said NSAID is selected from nabumetone, tiaramide, proquazone, bufexamac, flumizole, epirazole, tinoridine, timegadine, dapsone, aspirin, diflunisal, benorylate, fosfosal, diclofenac, alclofenac, fenclofenac, etodolac, indomethacin, sulindac, tolmetin, fentiazac, tilomisole, carprofen, fenbufen, flurbiprofen, ketoprofen, oxaprozin, suprofen, tiaprofenic acid, ibuprofen, naproxen, fenoprofen, indoprofen, pirprofen, flufenamic, mefenamic, meclofenamic, niflumic, oxyphenbutazone, phenylbutazone, apazone and feprazone, piroxicam, sudoxicam, isoxicam and tenoxicam.

5. The particles of claim 1 wherein said NSAID is selected from naproxen, indomethacin and ibuprofen.

6. The particles of claim 1 wherein said surface modifier is selected from polyvinylpyrrolidone and a block copolymer of ethylene oxide and propylene oxide.

7. Particles according to claim 1 consisting of naproxen having a block copolymer of ethylene oxide and propylene oxide adsorbed on the surface thereof in an amount sufficient to maintain an average particle size of less than about 400 nm.

8. Particles according to claim 1 consisting essentially of naproxen having polyvinylpyrrolidone adsorbed on the surface thereof in an amount sufficient to maintain an average particle size of less than about 400 nm.

9. A pharmaceutical composition comprising the particles of claim 1 and a pharmaceutically acceptable carrier.

10. A method of treating a mammal comprising administering to the mammal an effective amount of the pharmaceutical composition of claim 9.

11. A method of reducing gastric irritation following oral administration to a mammal of a pharmaceutical composition comprising an NSAID, said method comprising administering the pharmaceutical composition of claim 9.

12. A method of hastening onset of action following administration to a mammal of a pharmaceutical composition an NSAID, said method comprising administering the pharmaceutical composition of claim 9.

13. A method of hastening onset of action following administration to a mammal of pharmaceutical composition, said method comprising administering said pharmaceutical composition in the form of particles consisting essentially of 99.9–10% by weight of a crystalline drug substance having a solubility in water of less than 10 mg/ml, said drug substance having a non-crosslinked surface modifier adsorbed on the surface thereof in an amount of 0.1–90% by weight and sufficient to maintain an average particle size of less than about 400 nm.

* * * * *